United States Patent [19]

Hayashi et al.

[11] 4,207,332
[45] Jun. 10, 1980

[54] PROSTAGLANDIN I₂ ANALOGUES

[75] Inventors: Masaki Hayashi, Takatsuki; Yoshinobu Arai, Toyonaka; Katsuichi Shimoji; Yoshitaka Konishi, both of Takatsuki; Shuichi Ohuchida, Nishinomiya; Shinsuke Hashimoto, Nishinomiya, all of Japan

[73] Assignee: Ono Pharmaceutical Co., Ltd., Osaka, Japan

[21] Appl. No.: 944,164

[22] Filed: Sep. 20, 1978

[30] Foreign Application Priority Data

Sep. 22, 1977 [JP] Japan ................................ 52-113291

[51] Int. Cl.² .................... C07D 307/93; A61K 31/34
[52] U.S. Cl. .................................... 424/285; 542/426; 542/429; 260/346.22; 260/346.73
[58] Field of Search ..................... 260/346.22, 346.73; 560/103; 542/426, 429; 424/285

[56] References Cited
PUBLICATIONS

Corey et al., J.A.C.S., 99:6, Mar. 1977, pp. 2006–2008.

Primary Examiner—John M. Ford
Assistant Examiner—Bernard Dentz
Attorney, Agent, or Firm—Stevens, Davis, Miller & Mosher

[57] ABSTRACT

Prostaglandin analogues of the general formula:

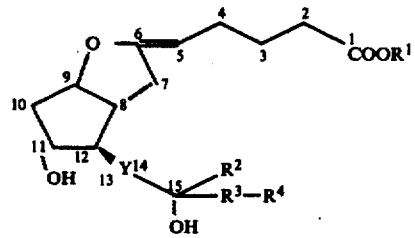

[wherein Y represents ethylene or trans-vinylene, $R^1$ represents a group $-C_mH_{2m}COOR^5$, $-C_nH_{2n}OR^6$ or

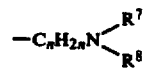

(wherein $R^5$ represents an alkyl group containing from 1 to 4 carbon atoms, $R^6$ represents a hydrogen atom or an alkyl group containing from 1 to 4 carbon atoms, $R^7$ and $R^8$, which may be the same or different, each represents an alkyl group containing from 1 to 4 carbon atoms, m represents an integer of from 1 to 12 and n represents an integer of from 2 to 12), $R^2$ represents a hydrogen atom or a methyl or ethyl group, $R^3$ represents a single bond, or an alkylene group containing from 1 to 4 carbon atoms, $R^4$ represents a hydrogen atom, an alkyl group containing from 1 to 8 carbon atoms, a cycloalkyl group containing from 4 to 7 carbon atoms in the ring, which may be unsubstituted or substituted by at least one alkyl group containing from 1 to 8 carbon atoms, or represents a phenyl or phenoxy group which may be unsubstituted or substituted by at least one chlorine atom, trifluoromethyl group or alkyl group containing from 1 to 3 carbon atoms, the wavy line attached to the carbon atoms in positions 11 and 15 represents α- or β-configuration, or mixtures thereof, and the double bond between $C_5$–$C_6$ is Z] and cyclodextrin clathrates thereof, and, when $R^1$ represents a group

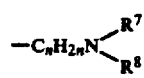

in which n, $R^7$ and $R^8$ are as hereinbefore defined, nontoxic acid addition salts thereof, are new compounds and possess characteristic prostaglandin-like properties.

21 Claims, No Drawings

PROSTAGLANDIN I₂ ANALOGUES

This invention relates to new prostaglandin I₂ (PGI₂) analogues, to a process for their preparation, and to pharmaceutical compositions containing them.

PGI₂ is a physiologically active natural substance having the following formula I:

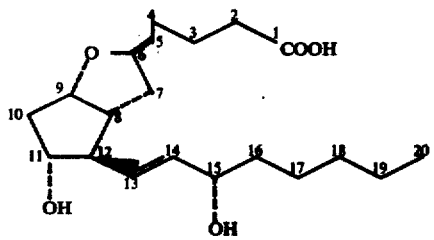

and its chemical name is (5Z,13E)-(9α,11α,15S)-6,9-epoxy-11,15-dihydroxyprosta-5,13-dienoic acid [Nature, 263, 663 (1976), Prostaglandins, 12, 685 (1976), ibid, 12, 915 (1976), ibid, 13, 3 (1977), ibid, 13, 375 (1977) and Chemical and Engineering News, Dec. 20, 17 (1976)].

It is well known that PGI₂ can be prepared by incubation of prostaglandin G₂ (PGG₂) or prostaglandin H₂ (PGH₂) with microsomal fractions prepared from thoracic aorta of swine, mesenteric artery of swine, rabbit aorta or the stomach fundus of rats. PGI₂ has a strong relaxing activity on the artery, which is peculiar to the artery and which does not operate on other smooth muscle. Furthermore, PGI₂ strongly inhibits arachidonic acid-induced blood platelet aggregation of the human.

Taking into consideration that thromboxane A₂, prepared by incubation of PGG₂ or PGH₂ with blood platelet microsome, has a contracting activity on the artery and an aggregating activity on blood platelets, the properties of PGI₂ heretofore mentioned show that PGI₂ fulfils a very important physiological part in a living body. PGI₂ may be useful in the treatment of arteriosclerosis, cardiac failure or thrombosis.

Natural PGI₂ is no unstable (being deactivated in a buffer solution at pH 7.6 after 20 minutes at 22° C., or after 10 minutes at 37° C.) that application of PGI₂ for medicinal purposes is difficult.

Widespread investigations have been carried out in order to discover processes for the chemical preparation of more stable analogues of PGI₂, and their products possessing the pharmacological properties of the 'natural' PGI₂ or one or more of such properties to an enhanced degree, or hitherto unknown pharmacological properties. As a result of extensive research and experimentation it has been discovered that in certain ester derivatives of PGI₂ and analogues thereof the properties of the 'natural' PGI₂ are, in some aspects of its activities, improved or modified.

The present invention accordingly provides new prostaglandin analogues of the general formula:

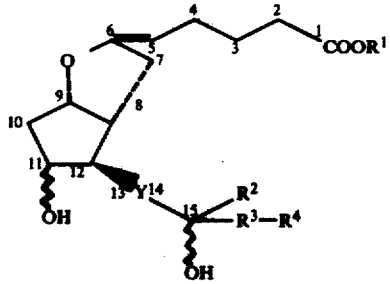

[wherein Y represents ethylene (i.e. —CH₂CH₂—) or, preferably, trans-vinylene (i.e.

$$\underset{H}{\overset{}{>}}C=C\underset{}{\overset{H}{<}} ),$$

R¹ represents a group —C$_m$H$_{2m}$COOR⁵, —C$_n$H$_{2n}$OR⁶ or

(wherein R⁵ represents a straight- or branched-chain alkyl group containing from 1 to 4 carbon atoms, R⁶ represents a hydrogen atom or a straight- or branched-chain alkyl group containing from 1 to 4 carbon atoms, R⁷ and R⁸, which may be the same or different, each represents a straight- or branched-chain alkyl group containing from 1 to 4 carbon atoms, m represents an integer of from 1 to 12 and n represents an integer of from 2 to 12), R² represents a methyl or ethyl group or, preferably, a hydrogen atom, R³ represents a single bond or a straight- or branched-chain alkylene group containing from 1 to 4 carbon atoms, R⁴ represents a hydrogen atom, a straight- or branched-chain alkyl group containing from 1 to 8 carbon atoms, a cycloalkyl group containing from 4 to 7 carbon atoms in the ring, which may be unsubstituted or substituted by at least one straight- or branched-chain alkyl group containing from 1 to 8 carbon atoms, or represents a phenyl or phenoxy group which may be unsubstituted or substituted by at least one chlorine atom, trifluoromethyl group or alkyl group containing from 1 to 3 carbon atoms, the wavy line attached to the carbon atoms in positions 11 and 15 represents α- or β-configuration (i.e. S- or R-configuration) or mixtures thereof, and the double bond between C₅–C₆ is Z] and cyclodextrin clathrates thereof and, when R¹ represents a group

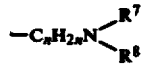

in which n, R⁷ and R⁸ are as hereinbefore defined, non-toxic acid addition salts thereof.

The present invention is concerned with all compounds of general formula II in the 'natural' form or its enantiomeric form, or mixtures thereof, more particularly the racemic form, consisting of equimolecular mixtures of 'natural' form and its enantiomeric form.

As will be apparent to those skilled in the art, the compounds depicted in general formula II have at least five centres of chirality, these five centres of chirality being at the C-8, C-9, C-11, C-12 and C-15 carbon atoms. Still further centres of chirality may occur when $R^4$, $R^5$, $R^6$, $R^7$ or $R^8$ is a branched-chain alkyl group or $R^3$ or a —$C_mH_{2m}$— or —$C_nH_{2n}$— moiety is a branched-chain alkylene group. The presence of chirality leads as is well known to the existence of isomerism. However, the compounds of general formula II all have such a configuration that the substituent groups attached to the alicyclic ring carbon atoms in the positions identified as 8 and 9 are cis with respect to each other and that the substituent groups attached to the carbon atoms in the positions identified as 8 and 12 are trans with respect to each other.

Accordingly, all isomers of general formula II and mixtures thereof which have those substituent groups attached to the ring carbon atoms in positions 8 and 9 in the cis-configuration, those attached in positions 8 and 12 in the trans-configuration and have hydroxy groups as depicted in the 11- and 15-positions are to be considered within the scope of general formula II. Preferably the hydroxy groups attached to the C-11 and C-15 carbon atoms are in α-configuration.

Preferably the grouping —$R^3$—$R^4$ represents, for example, n-pentyl, 1-methylpentyl, 2-methylpentyl, 3-methylpentyl, 4-methylpentyl, 1,1-dimethylpentyl, 1,2-dimethylpentyl, 1,4-dimethylpentyl, 1-ethylpentyl, 2-ethylpentyl, 1-propylpentyl, 2-propylpentyl, n-hexyl, 1-methylhexyl, 2-methylhexyl, 1,1-dimethylhexyl, 1-ethylhexyl, 2-ethylhexyl, n-heptyl, 2-ethylheptyl, n-nonyl, n-undecyl, cyclobutyl, (1-propyl)cyclobutyl, (1-butyl)-cyclobutyl, (1-pentyl)cyclobutyl, (2-propyl)-cyclobutyl, (3-ethyl)cyclobutyl, (3-propyl)cyclobutyl, cyclopentyl, 1-cyclopentylethyl, 2-cyclopentylethyl, 2-cyclopentylpropyl, (3-ethyl)cyclopentyl, (3-propyl)-cyclopentyl, (3-butyl)cyclopentyl, (1-methyl-3-propyl)-cyclopentyl, (2-methyl-3-propyl)cyclopentyl, cyclohexyl, (3-ethyl)-cyclohexyl, (4-methyl)cyclohexyl, (4-ethyl)cyclohexyl, (4-propyl)cyclohexyl, (2,6-dimethyl)-cyclohexyl, cyclohexylmethyl, (1-methyl)cyclohexylmethyl, 1-cyclohexylethyl, 2-cyclohexylethyl, (1-methyl-1-cyclohexyl)ethyl, 1-cycloheptylethyl, phenyl, benzyl, α-phenylethyl, β-phenylethyl, phenoxymethyl, (3-chlorophenoxy)methyl, (4-chlorophenoxy)methyl and (3-trifluoromethylphenoxy)methyl. The grouping —$R^3$—$R^4$ most preferably represents n-pentyl.

The alkyl groups represented by $R^5$, $R^6$, $R^7$ or $R^8$ may be methyl, ethyl, n-propyl, isopropyl, n-butyl, isobutyl, sec-butyl and tert-butyl.

The straight- or branched-chain alkylene group represented by —$C_mH_{2m}$— and —$C_nH_{2m}$— may be methylene (when m in the —$C_mH_{2m}$— moiety is 1), ethylene, trimethylene, tetramethylene, pentamethylene, hexamethylene, heptamethylene, octamethylene, nonamethylene, decamethylene, undecamethylene, dodecamethylene, and the isomers thereof, with straight-chain alkylene groups being preferable.

When $R^1$ represents a group —$C_mH_{2m}COOR^5$, m preferably represents an integer from 1 to 9 and $R^5$ preferably represents a straight- or branched-chain alkyl group containing from 1 to 4 carbons, e.g. ethyl. When $R^1$ represents a group —$C_nH_{2n}OR^6$, n preferably represents an integer from 2 to 8 and $R^6$ preferably represents a hydrogen atom or a straight- or branched-chain alkyl group containing from 1 to 4 carbon atoms, e.g. propyl. When $R^1$ represents a group

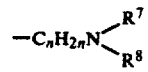

n preferably represents 2 and $R^7$ and $R^8$ both represent a straight- or branched-chain alkyl group containing from 1 to 4 carbon atoms, e.g. methyl or ethyl.

According to a feature of the present invention, the prostaglandin analogues of general formula II, wherein the various symbols are as hereinbefore defined, are prepared by dehydrobromination of a compound of the general formula:

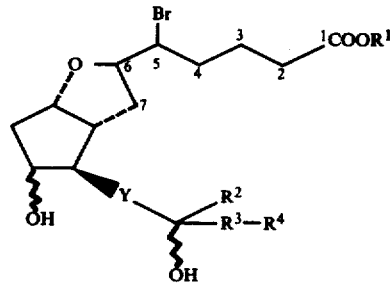

wherein the absolute configurations of $C_5$ and $C_6$ are (5S, 6S) or (5R, 6R), or a mixture thereof, and the various symbols are as hereinbefore defined.

The dehydrobromination may be carried out with a known dehydrobromination reagent, for example, a bicycloamine such as 1,5-diazabicyclo[5.4.0]undecene-5 (DBU), 1,5-diazabicyclo[4.3.0]nonene-5 (DBN) or 1,4-diazabicyclo[2.2.2]octane (DABCO), or an alkali metal, e.g. sodium or potassium, alcholate containing from 1 to 4 carbon atoms. The reaction may be carried out at a temperature from 40° C. to 110° C., preferably at a temperature from 40° C. to 80° C. and, when the reagent is a bicycloamine, optionally in the presence of an inert organic solvent, preferably in the absence of an inert organic solvent or in the presence of toluene or when the reagent is an alcoholate, in the presence of the corresponding alkanol.

Compounds of general formula III may be prepared by the hydrolysis to hydroxy groups of the groups $OR^9$ of a compound of the general formula:

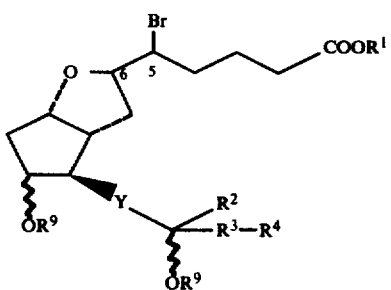

wherein $R^9$ represents a tetrahydropyran-2-yl group, unsubstituted or substituted by at least one alkyl group, or a tetrahydrofuran-2-yl or 1-ethoxyethyl group, the absolute configurations of $C_5$ and $C_6$ are (5S, 6S) or (5R, 6R), or a mixture thereof, and the other symbols are as hereinbefore defined.

The groups $OR^9$ of the compounds of general formula IV may be converted to hydroxy groups by mild acidic hydrolysis (1) with an aqueous solution of an organic acid such as acetic acid, propionic acid, oxalic acid, or p-toluenesulphonic acid, or an aqueous solution of an inorganic acid such as hydrochloric or sulphuric acid, advantageously in the presence of an inert organic solvent miscible with water, e.g. a lower alkanol such as methanol or ethanol, preferably methanol, or an ether such as 1,2-dimethoxyethane, dioxan, or tetrahydrofuran (preferably tetrahydrofuran), at a temperature ranging from ambient to 75° C., or (2) with an anhydrous solution of an organic acid such as p-toluenesulphonic acid or trifluoroacetic acid in a lower alkanol such as methanol or ethanol at a temperature ranging from 10° to 45° C. Advantageously the mild acidic hydrolysis may be carried out with a mixture of dilute hydrochloric acid and tetrahydrofuran, a mixture of dilute hydrochloric acid and methanol, a mixture of acetic acid, water and tetrahydrofuran, or a mixture of p-toluenesulphonic acid and absolute methanol.

Compounds of general formulae III and IV may be prepared by the bromination and simultaneous cyclization of a compound of the general formula:

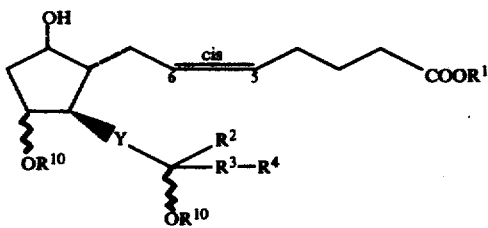

V

[wherein $R^{10}$ represents a hydrogen atom or a tetrahydropyran-2-yl group, unsubstituted or substituted by at least one alkyl group, or a tetrahydrofuran-2-yl or 1-ethoxyethyl group, the double bond between $C_5$–$C_6$ is cis (i.e. Z), and the other symbols are as hereinbefore defined] with N-bromosuccinimide or N-bromoacetamide in an aprotic organic solvent, e.g. methylene chloride, chloroform, carbon tetrachloride, diethyl ether, N,N-dimethylformamide or tetrahydrofuran, or a mixture of two or more of them at a temperature of from −30° C. to 70° C. The product of general formula III or IV thus obtained is a mixture of isomers in which the absolute configurations of $C_5$ and $C_6$ are (5S, 6S) and (5R, 6R). However, as either isomer of general formula III yields after dehydrobromination, a product of general formula II in which the double bond between $C_5$–$C_6$ is Z, it is not necessary to separate the isomers unless such separation is particularly desired.

The ester compounds of general formula V may be obtained by the esterification, by methods known per se, of a carboxylic acid of the general formula:

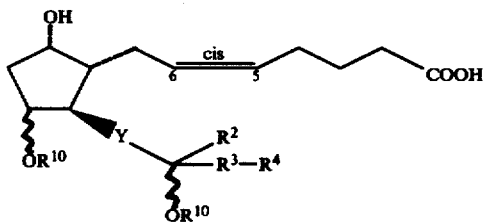

VI (wherein the double bond between $C_5$–$C_6$ is cis and the various symbols are as hereinbefore defined) using an alcohol of the general formula $R^1OH$, wherein $R^1$ is as hereinbefore defined. By the expression "methods known per se" as used in this specification is meant methods heretofore used or described in the chemical literature.

The esters of general formula V may be prepared from the corresponding acids of general formula VI, for example, by reaction with (i) the appropriate alcohol in the presence of dicyclohexylcarbodiimide as condensing agent, or (ii) the appropriate alcohol following formation of a mixed anhydride by adding a tertiary amine and a pivaloyl halide or an alkylsulphonyl or arylsulphonyl halide (cf. our British Pat. Nos. 1,362,956 and 1,364,125).

The preparation of esters of general formula V using dicyclohexylcarbodiimide is carried out by reacting the corresponding acid of general formula VI with an alcohol $R^1OH$, wherein $R^1$ is as hereinbefore defined, in an inert organic solvent such as a halogenated hydrocarbon, e.g. chloroform or methylene chloride, in the presence of a base, such as pyridine or picoline, preferably pyridine, at a temperature of from 0° C. to ambient.

The preparation of esters of general formula V using a pivaloyl halide (e.g. pivaloyl chloride), an arylsulphonyl halide (e.g. p-toluenesulphonyl chloride or benzenesulphonyl chloride), or an alkylsulphonyl halide (e.g. methanesulphonyl chloride or ethanesulphonyl chloride) is carried out by reacting an acid of general formula VI with a tertiary amine, e.g. triethylamine or pyridine, and a pivaloyl halide, arylsulphonyl halide or alkylsulphonyl halide in the presence or absence of an inert organic solvent such as a halogenated hydrocarbon (e.g. chloroform or methylene chloride) or diethyl ether to prepare a mixed acid anhydride of the acid of general formula VI, and adding thereto, at a temperature from 0° C. to ambient, an alcohol $R^1OH$, wherein $R^1$ is as hereinbefore defined, to obtain the ester of general formula V.

Compounds of general formulae III and IV, wherein the various symbols are as hereinbefore defined, may also be prepared from compounds of the general formula:

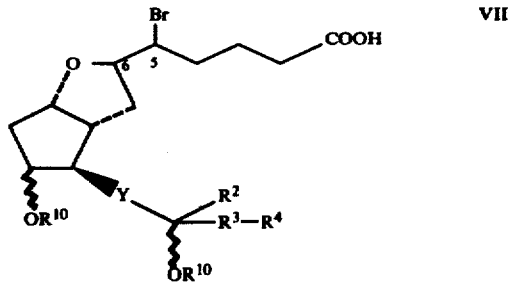

VII

[wherein the absolute configurations of $C_5$ and $C_6$ are (5S, 6S) or (5R, 6R), or a mixture thereof, and the various symbols are as hereinbefore defined] by means heretofore mentioned for the conversion of compounds of general formula VI to those of general formula V.

Compounds of general formula VII may be prepared from compounds of general formula VI by means heretofore mentioned for the conversion of compounds of general formula V to those of general formulae III and IV.

Starting materials of general formula VI may be prepared by the methods described in the following patent specifications and applications, or obvious modifications thereof:

(1) when $R^2$ is a hydrogen atom or a methyl or ethyl group and the grouping —$R^3$—$R^4$ is a straight- or branched-chain alkyl group, as described in Japanese Patent Kokai Nos. 49-124048, 49-134656, 50-13362, 50-25549, 50-101340 and 51-68547, British Pat. Nos. 1,398,291, 1,450,691, 1,464,916 and 1,483,240, and U.S. Pat. Nos. 3,962,312, 3,966,792 and 4,024,174;

(2) when $R^2$ is a hydrogen atom or a methyl or ethyl group, $R^3$ is a single bond or a straight- or branched-chain alkylene group and $R^4$ is an unsubstituted or substituted cycloalkyl group, as described in Japanese Patent Kokai Nos. 50-13364, 50-25549, 50-148339 and 51-68547, British Pat. Nos. 1,450,691, 1,464,916, 1,488,141, 1,483,240 and 1,484,210, British Patent Applications Nos. 30072/75 and 18651/76, U.S. Pat. Nos. 3,962,312, 3,966,792, 4,034,003, 4,024,174, 4,045,468 and 4,087,620 and Belgian Pat. No. 844,256;

(3) when $R^2$ is a hydrogen atom or a methyl or ethyl group, $R^3$ is a single bond or a straight- or branched-chain alkylene group and $R^4$ is an unsubstituted or substituted phenyl group, as described in Japanese Patent Kokai Nos. 50-13364, 50-25549 and 51-68547, British Pat. Nos. 1,450,691 and 1,483,240 and U.S. Pat. Nos. 3,962,312 and 4,024,174;

(4) when $R^2$ is a hydrogen atom or a methyl or ethyl group, $R^3$ is a single bond or a straight- or branched-chain alkylene group and $R^4$ is an unsubstituted or substituted phenoxy group, as described in Japanese Patent Kokai No. 51-59841 or 52-25745, British Pat. No. 1,521,747, U.S. Pat. No. 4,065,632 and Belgian Pat. No. 845348;

(5) when $R^2$ is a hydrogen atom, $R^3$ is a single bond and $R^4$ is a hydrogen atom, from compounds of general formula VIII depicted hereafter, by the series of reactions depicted schematically below in Scheme A, wherein $R^{11}$ represents an alkanoyl group containing from 2 to 5 carbon atoms and the other symbols are as hereinbefore defined.

SCHEME A

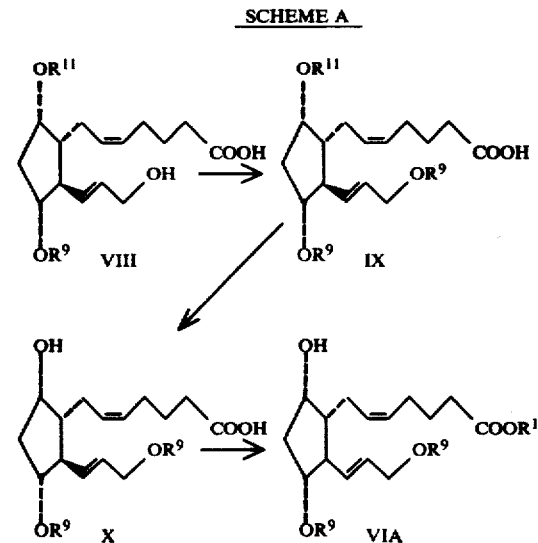

Compounds of the general formula VIII may be converted into compounds of general formula IX by reaction with a dihydropyran, dihydrofuran or ethyl vinyl ether in an inert solvent, e.g. methylene chloride, in the presence of a condensing agent, e.g. p-toluenesulphonic acid.

Compounds of the general formula IX may be converted into compounds of the general formula X by hydrolysis under alkaline conditions, which may be effected with anhydrous potassium carbonate in an anhydrous alkanol containing at most four carbon atoms, preferably absolute methanol.

Compounds of general formula X may be converted to compounds of general formula VIA by means heretofore described for the conversion of compounds of general formula VI to those of general formula V.

Compounds of general formula VIII may be prepared as described in British Pat. No. 1,482,928.

Cyclodextrin clathrates of the prostaglandin analogues of general formula II may be prepared by dissolving the cyclodextrin in water or an organic solvent which is miscible with water, in the presence of triethylamine, and adding to the solution the prostaglandin analogue in a water-miscible organic solvent. The mixture is then heated and the desired cyclodextrin clathrate product isolated by concentrating the mixture under reduced pressure or by cooling and separating the product by filtration or decantation. The ratio of organic solvent to water may be varied according to the solubilities of the starting materials and products. Preferably the temperature is not allowed to exceed 70° C. during the preparation of the cyclodextrin clathrates. α-, β- or γ-Cyclodextrins or mixtures thereof may be used in the preparation of the cyclodextrin clathrates. Conversion into their cyclodextrin clathrates serves to increase the stability of the prostaglandin analogues.

The prostaglandin $I_2$ analogues of general formula II, wherein $R^1$ represents a group $$-C_nH_{2n}N\begin{matrix}R^7\\R^8\end{matrix}$$

in which n, $R^7$ and $R^8$ are as hereinbefore defined, may, if desired, be converted by methods known per se into acid addition salts, which are preferably non-toxic. By the term "non-toxic acid addition salts" as used in this specification is meant salts the anions of which are relatively innocuous to the animal organism when used in therapeutic doses so that the beneficial pharmacological properties of the compounds of general formula II are not vitiated by side effects ascribable to those anions. Suitable non-toxic acid addition salts are those formed with inorganic acids (such as hydrochlorides and sulphates) and with organic acids (such as acetates, propionates, succinates and benzoates).

The prostaglandin $I_2$ analogues of general formula II and their cyclodextrin clathrates and, when $R^1$ in general formula II represents a group $$-C_nH_{2n}N\begin{matrix}R^7\\R^8\end{matrix}$$

in which n, $R^7$ and $R^8$ are as hereinbefore defined, their non-toxic acid addition salts, possess the valuable pharmacological properties typical of the prostaglandins in a selective fashion, in particular relaxing activity of artery, and inhibitory activity on blood platelet aggregation, and hence they are useful in the treatment of hypertension and disorders of the peripheral circulation and in the prevention and treatment of cerebral thrombosis, myocardial infarction and arteriosclerosis.

For example, in standard laboratory tests, (i) by intravenous administration to the allobarbitalanaesthetized dog, (5Z,13E)-(9α,11α,15S)-6,9-epoxy-11,15-dihydroxyprosta-5,13-dienoic acid 2-(N,N-diethylamino)ethyl ester produces a fall in blood pressure of 26 mm Hg and 60 mm Hg lasting 6 and 12 minutes at the doses of 1 and 4 μg/kg animal body weight, respectively, (5Z,13E)-(9α,11α,15S)-6,9-epoxy-11,15-dihydroxyprosta-5,13-dienoic acid 2-propoxyethyl ester produces a fall in blood pressure of 8 mm Hg and 42 mm Hg lasting 7 and 8 minutes at the doses of 0.2 and 0.5 μg/kg animal body weight, respectively, (5Z,13E)-(9α,11α,15S)-6,9-epoxy-11,15-dihydroxyprosta-5,13-dienoic acid ethoxycarbonylmethyl ester produces a fall in blood pressure of 26 mm Hg and 64 mm Hg lasting 8 and 16 minutes at the doses of 1 and 2 μg/kg animal body weight, respectively, (5Z,13E)-(9α,11α,15S)-6,9-epoxy-11,15-dihydroxyprosta-5,13-dienoic acid 5-hydroxypentyl ester produces a fall in blood pressure of 36 mm Hg and 62 mm Hg lasting 23 and 23 minutes at the doses of 0.3 and 1.0 μg/kg animal body weight, respectively, (5Z,13E)-(9α,11α,15S)-6,9-epoxy-11,15-dihydroxyprosta-5,13-dienoic acid 2-hydroxyethyl ester produces a fall in blood pressure of 20 mm Hg and 46 mm Hg lasting 3 and 6 minutes at the doses of 0.1 and 0.2 μg/kg animal body weight, respectively, (5Z,13E)-(9α,11α,15S)-6,9-epoxy-11,15-dihydroxyprosta-5,13-dienoic acid 8-hydroxyoctyl ester produces a fall in blood pressure of 20 mm Hg and 32 mm Hg lasting 9 and 15 minutes at the doses of 1 and 2 μg/kg animal body weight, respectively, and (5Z,13E)-(9α,11α,15S)-6,9-epoxy-11,15-dihydroxyprosta-5,13-dienoic acid 2-(N,N-dimethylamino)ethyl ester produces a fall in blood pressure of 20 mm Hg and 35 mm Hg lasting 8 and 12 minutes at the doses of 2 and 4 μg/kg animal body weight, respectively, and (ii) (5Z,13E)-(9α,11α,15S)-6,9-epoxy-11,15-dihydroxyprosta-5,13-dienoic acid 2-(N,N-diethylamino)ethyl ester, (5Z,13E)-(9α,11α,15S)-6,9-epoxy-11,15-dihydroxyprosta-5,13-dienoic acid 2-propoxyethyl ester, (5Z,13E)-(9α,11α,15S)-6,9-epoxy-11,15-dihydroxyprosta-5,13-dienoic acid ethoxycarbonylmethyl ester, (5Z,13E)-(9α,11α,15S)-6,9-epoxy-11,15-dihydroxyprosta-5,13-dienoic acid 5-hydroxypentyl ester, (5Z,13E)-(9α,11α,15S)-6,9-epoxy-11,15-dihydroxyprosta-5,13-dienoic acid 2-hydroxyethyl ester, (5Z,13E)-(9α,11α,15S)-6,9-epoxy-11,15-dihydroxyprosta-5,13-dienoic acid 8-hydroxyoctyl ester and (5Z,13E)-(9α,11α,15S)-6,9-epoxy-11,15-dihydroxyprosta-5,13-dienoic acid 2-(N,N-dimethylamino)ethyl ester produce a 50% inhibition of adenosine diphosphate-induced blood platelet aggregation in platelet-rich plasma of rats at the concentrations of $1.85 \times 10^{-3}$, $1.75 \times 10^{-3}$, $1.60 \times 10^{-2}$, $1.9 \times 10^{-3}$, $2.55 \times 10^{-3}$, $3.4 \times 10^{-3}$ and $4.2 \times 10^{-3}$ μg/ml, respectively, in comparison with controls.

Examples of PGI$_2$ compounds of general formula II according to the present invention are esters of the following, in which the ester moiety is a group R$^1$ as hereinbefore defined: PGI$_2$, 15-methyl-PGI$_2$, 16-methyl-PGI$_2$, 17-methyl-PGI$_2$, 18-methyl-PGI$_2$, 19-methyl-PGI$_2$, 20-methyl-PGI$_2$, 15,16-dimethyl-PGI$_2$, 16,16-dimethyl-PGI$_2$, 16,17-dimethyl-PGI$_2$, 16,19-dimethyl-PGI$_2$, 16-ethyl-PGI$_2$, 17-ethyl-PGI$_2$, 20-ethyl-PGI$_2$, 16-propyl-PGI$_2$, 17-propyl-PGI$_2$, 16,20-dimethyl-PGI$_2$, 17,20-dimethyl-PGI$_2$, 16,16,20-trimethyl-PGI$_2$, 17-methyl-20-ethyl-PGI$_2$, 16-ethyl-20-methyl-PGI$_2$, 17-methyl-20-methyl-PGI$_2$, 17,20-diethyl-PGI$_2$, 20-butyl-PGI$_2$, 20-hexyl-PGI$_2$, 15-cyclobutyl-16,17,18,19,20-pentanor-PGI$_2$, 15-(1-propyl)cyclobutyl-16,17,18,19,20-pentanor-PGI$_2$, 15-(1-butyl)cyclobutyl-16,17,18,19,20-pentanor-PGI$_2$, 15-(1-pentyl)cyclobutyl-16,17,18,19,20-pentanor-PGI$_2$, 15-(2-propyl)cyclobutyl-16,17,18,19,20-pentanor-PGI$_2$, 15-(3-ethyl)cyclobutyl-16,17,18,19,20-pentanor-PGI$_2$, 15-(3-propyl)cyclobutyl-16,17,18,19,20-pentanor-PGI$_2$, 15-cyclopentyl-16,17,18,19,20-pentanor-PGI$_2$, 16-cyclopentyl-18,19,20-trinor-PGI$_2$, 17-cyclopentyl-18,19,20-trinor-PGI$_2$, 17-cyclopentyl-19,20-dinor-PGI$_2$, 15-(3-ethyl)cyclopentyl-16,17,18,19,20-pentanor-PGI$_2$, 15-(3-propyl)cyclopentyl-16,17,18,19,20-pentanor-PGI$_2$, 15-(3-butyl)cyclopentyl-16,17,18,19,20-pentanor-PGI$_2$, 15-(1-methyl-3-propyl)cyclopentyl-16,17,18,19,20-pentanor-PGI$_2$, 15-(2-methyl-3-propyl)cyclopentyl-16,17,18,19,20-pentanor-PGI$_2$, 15-cyclohexyl-16,17,18,19,20-pentanor-PGI$_2$, 15-(3-ethyl)cyclohexyl-16,17,18,19,20-pentanor-PGI$_2$, 15-(4-methyl)cyclohexyl-16,17,18,19,20-pentanor-PGI$_2$, 15-(4-ethyl)cyclohexyl-16,17,18,19,20-pentanor-PGI$_2$, 15-(4-propyl)cyclohexyl-16,17,18,19,20-pentanor-PGI$_2$, 15-(2,6-dimethyl)cyclohexyl-16,17,18,19,20-pentanor-PGI$_2$, 16-cyclohexyl-17,18,19,20-tetranor-PGI$_2$, 16-(1-methyl)cyclohexyl-17,18,19,20-tetranor-PGI$_2$, 16-cyclohexyl-18,19,20-trinor-PGI$_2$, 17-cyclohexyl-18,19,20-trinor-PGI$_2$, 16-methyl-16-cyclohexyl-18,19,20-trinor-PGI$_2$, 16-cycloheptyl-18,19,20-trinor-PGI$_2$, 15-phenyl-16,17,18,19,20-pentanor-PGI$_2$, 16-phenyl-17,18,19,20-tetranor-PGI$_2$, 16-phenyl-18,19,20-trinor-PGI$_2$, 17-phenyl-18,19,20-trinor-PGI$_2$, 16-phenoxy-17,18,19,20-tetranor-PGI$_2$, 16-(3-chlorophenoxy)-17,18,19,20-tetranor-PGI$_2$, 16-(4-chlorophenoxy)-17,18,19,20-tetranor-PGI$_2$ and 16-(3-trifluoromethylphenoxy)-17,18,19,20-tetranor-PGI$_2$.

Preferred PGI$_2$ compounds of general formula II according to the present invention are the 2-(N,N-diethylamino)ethyl, 5-hydroxypentyl, 2-propoxyethyl, ethoxycarbonylmethyl, ethoxycarbonylnonyl, 8-hydroxyoctyl, 2-(N,N-dimethylamino)ethyl and 2-hydroxyethyl esters of PGI$_2$.

Compounds of general formulae III and IV are new compounds and as such constitute a feature of the present invention.

The following Reference Examples and Examples illustrate, but do not limit, the preparation of new prostaglandin analogues of the present invention. In them 'TLC', 'IR' and 'NMR' represent respectively 'Thin layer chromatography', 'Infrared absorption spectrum', and 'Nuclear magnetic resonance spectrum'. Where solvent ratios are specified in chromatographic separations, the ratios are by volume. PGF$_{2α}$, referred to in the Reference Examples and Examples, is (5Z,13E)-(9α,11α,15S)-9,11,15-trihydroxyprosta-5,13-dienoic acid.

REFERENCE EXAMPLE 1

PGF$_{2α}$ 2-(N,N-diethylamino)ethyl ester 0.202 ml of triethylamine and 0.175 ml of pivaloyl chloride were added to a solution of 540 mg of PGF$_{2α}$ in 12 ml of methylene chloride, and the mixture was stirred for 10 minutes at ambient temperature. To the solution obtained were added 2.4 ml of 2-(N,N-diethylamino)ethanol and 1.17 mg of pyridine, and the resulting mixture was stirred for 2 hours at ambient temperature. The solution obtained was diluted with ethyl acetate, washed with an aqueous solution of sodium bicarbonate, water, and an aqueous solution of sodium chloride, dried over magnesium sulphate and concentrated under reduced pressure. The residue obtained was purified by column chromatography on silica gel using a mixture of cyclohexane and ethyl acetate (2:3) as eluent to give 388 mg of the title compound having the following physical characteristics. TLC (developing solvent, chloroform:tetrahydrofuran:acetic acid = 10:2:1):Rf=0.20; IR (liquid film):$\nu$=3400, 1735, 1460, 1160, 970 cm$^{-1}$; NMR (CDCl$_3$ solution): $\delta$=5.65–5.20 (4H, m), 4.14 (2H, t), 4.30–3.80 (3H, m), 2.70 (2H, t), 2.58 (4H, q), 1.03 (6H, t), 1.00–0.78 (3H, m).

EXAMPLE 1

(13E)-(5RS,6RS,9α,11α,15S)-5-Bromo-6,9-epoxy-11,15-dihydroxyprost-13-enoic acid 2-(N,N-diethylamino)ethyl ester To a suspension of 160 mg of N-bromosuccinimide in 5 ml of methylene chloride was added dropwise under a nitrogen atmosphere a solution of 340 mg of the PGF$_{2\alpha}$ 2-(N,N-diethylamino)ethyl ester (prepared as described in Reference Example 1) in 3.6 ml of a mixture of methylene chloride and N,N-dimethylformamide (5:1) at −20° C. to −10° C., and the resulting solution was stirred for 30 minutes at the same temperature. The solution was then poured into cold water and extracted with diethyl ether. The extract was washed with water and an aqueous solution of sodium chloride, dried over magnesium sulphate and concentrated under reduced pressure. The residue was purified by column chromatography on silica gel using a mixture of acetone and ethyl acetate (1:5) as eluent to give 321 mg of the title compound having the following physical characteristics. TLC (developing solvent, diethyl ether:acetone=3:1 containing 0.1% of triethylamine; silica gel plate pre-treated with diethyl ether containing 5% v/v of triethylamine): Rf=0.28; IR (liquid film): $\nu$=3400, 1740, 1450, 1180, 975 cm$^{-1}$; NMR (CDCl$_3$ solution): $\delta$=5.70–5.42 (2H, m), 4.65–4.40 (1H, m), 4.15 (2H, t), 4.30–3.60 (4H, m), 3.10 (2H, broad s), 2.70 (2H, t), 2.58 (4H, q), 1.03 (6H, t), 1.00–0.78 (3H, m).

EXAMPLE 2

(5Z,13E)-(9α,11α,15S)-6,9-Epoxy-11,15-dihydroxyprosta-5,13-dienoic acid 2-(N,N-diethylamino)ethyl ester [PGI$_2$ 2-(N,N-diethylamino)ethyl ester]

123 mg of (13E)-(5RS,6RS,9α,11α,15S)-5-bromo-6,9-epoxy-11,15-dihydroxyprost-13-enoic acid 2-(N,N-diethylamino)ethyl ester (prepared as described in Example 1) and 0.4 ml of DBU (1,5-diazabicyclo[5.4.0]-undecene-5) were stirred at 50°–60° C. for 3 hours under a nitrogen atmosphere. The solution obtained was cooled to 0°–5° C., 2.5 ml of 1 N hydrochloric acid and 2 ml of a phosphate buffer with a pH of 6.86 cooled to 0°–5° C., were added, and the mixture was extracted with diethyl ether. The extract was washed with water and an aqueous solution of sodium chloride, dried over magnesium sulphate and concentrated under reduced pressure. The residue was purified by column chromatography on silica gel using as eluent a mixture of diethyl ether and acetone (6:1) containing 0.1% v/v of triethylamine to give 30 mg of the title compound having the following physical characteristics.

TLC (developing solvent, diethyl ether:acetone=3:1 containing 0.1% v/v of triethylamine; silica gel plate pre-treated with methylene chloride containing 5% v/v of triethylamine)- Rf=0.34;

IR (liquid film): $\nu$=3450, 1740, 1695, 1165, 970 cm$^{-1}$;

NMR (CDCl$_3$ solution): $\delta$=5.60–5.40 (2H, m), 4.67–4.45 (1H, m), 4.14 (2H, t), 4.25–3.65 (3H, m), 3.33 (2H, broad s), 2.70 (2H, t), 2.58 (4H, q), 1.03 (6H, t), 1.00 - 0.78 (3H, m).

REFERENCE EXAMPLE 2

PGF$_{2\alpha}$5-hydroxypentyl ester 0.5 ml of triethylamine and 0.44 ml of pivaloyl chloride were added to a solution of 1.051 g of PGF$_{2\alpha}$ in 20 ml of methylene chloride, and the mixture was stirred for 10 minutes at ambient temperature. To the solution obtained were added 4.7 ml of pentane-1,5-diol and 2.9 ml of pyridine and the mixture was stirred for 3 hours at ambient temperature. The solution obtained was washed with water, an aqueous solution of sodium bicarbonate, water, and an aqueous solution of sodium chloride, dried over magnesium sulphate and concentrated under reduced pressure. The residue was purified by column chromatography on silica gel using as eluent ethyl acetate containing 1% v/v of methanol to give 725 mg of the title compound having the following physical characteristics.

TLC (developing solvent, ethyl acetate:formic acid = 400:5): Rf=0.26;

IR (liquid film): $\nu$=3380, 1730, 1250, 1060, 980 cm$^{-1}$;

NMR (CDCl$_3$ solution): $\delta$=5.7–5.1 (4H, m), 4.3–3.0 (11H, m), 1.05–0.70 (3H, t).

EXAMPLE 3

(13E)-(5RS,6RS,9α,11α,15S)-5-Bromo-6,9-epoxy-11,15-dihydroxyprost-13-enoic acid 5-hydroxypentyl ester 303 mg of N-bromosuccinimide were added to a solution of 683 mg of PGF$_{2\alpha}$5-hydroxypentyl ester (prepared as described in Reference Example 2) in a mixture of 12 ml of chloroform and 3 ml of tetrahydrofuran under a nitrogen atmosphere, and the reaction mixture was stirred for 2 hours at ambient temperature. The solution obtained was poured into water and extracted with diethyl ether. The extract was washed with water and an aqueous solution of sodium chloride, dried over magnesium sulphate and concentrated under reduced pressure. The residue was purified by column chromatography on silica gel using as eluent a mixture of ethyl acetate and cyclohexane (5:1) to give 652 mg of the title compound having the following physical characteristics.

TLC (developing solvent, chloroform:tetrahydrofuran: acetic acid = 10:2:1): Rf=0.15;

IR (liquid film): $\nu$=3400, 1730, 970 cm$^{-1}$;

NMR (CDCl$_3$ solution): $\delta$=5.6–5.3 (2H, m), 4.7–3.2 (9H, m), 1.0–0.7 (3H, t).

EXAMPLE 4

(5Z,13E)-(9α,11α,15S)-6,9-Epoxy-11,15-dihydroxyprosta-5,13-dienoic acid 5-hydroxypentyl ester [PGI$_2$ 5-hydroxypentyl ester]

197 mg of (13E)-(5RS,6RS,9α,11α,15S)-5-bromo-6,9-epoxy-11,15-dihydroxyprost-13-enoic acid 5-hydroxypentyl ester (prepared as described in Example 3) and 0.66 ml of DBU were stirred for 3 hours at 50°–60° C. under a nitrogen atmosphere. The solution obtained was cooled to 0°–5° C., 3.3 ml of 1 N hydrochloric acid and 3.3 ml of a phosphate buffer with a pH of 6.86, cooled to 0°–5° C., were added and the mixture was extracted with diethyl ether. The extract was dried over magnesium sulphate and concentrated under reduced pressure. The residue was purified by column chromatography on "Florisil" (an activated magnesium silicate: "Florisil" is a registered Trade Mark of Florin Co.) using as eluent ethyl acetate containing 0.1% v/v of triethylamine to give 108 mg of the title compound having the following physical characteristics.

TLC (developing solvent, diethyl ether:acetone=3:1 containing 0.1% v/v of triethylamine; silica gel plate pre-treated with diethyl ether containing 5% v/v of triethylamine): Rf=0.25;

IR (liquid film): $\nu = 3400, 1735, 1700, 970$ cm$^{-1}$;

NMR (CDCl$_3$ solution): $\delta = 5.65-5.40$ (2H, m), 4.75-3.30 (8H, m), 1.05-0.70 (3H, m).

REFERENCE EXAMPLE 3

PGF$_{2\alpha}$ 2-propoxyethyl ester 0.43 ml of triethylamine and 0.38 ml of pivaloyl chloride were added to a solution of 914 mg of PGF$_{2\alpha}$ in 15 ml of methylene chloride, and the mixture was stirred for 10 minutes at ambient temperature. To the solution obtained were added 4 ml of 2-propoxyethanol and 2.5 ml of pyridine, and the reaction mixture was stirred for 2.5 hours at ambient temperature. The solution obtained was diluted with ethyl acetate, washed with water, an aqueous solution of sodium bicarbonate, water, and an aqueous solution of sodium chloride, dried over magnesium sulphate and concentrated under reduced pressure. The residue was purified by column chromatography on silica gel using as eluent a mixture of cyclohexane and ethyl acetate (1:2) to give 619 mg of the title compound having the following physical characteristics.

TLC (developing solvent, chloroform:tetrahydrofuran: acetic acid=10:2:1): Rf=0.17;

IR (liquid film): $\nu = 3370, 1730, 1125, 970$ cm$^{-1}$;

NMR (CDCl$_3$ solution): $\delta = 5.7-5.1$ (4H, m), 4.4-3.2 (9H, m), 1.07-0.55 (6H, m).

EXAMPLE 5

(13E)-(5RS,6RS,9α,11α,15S)-5-Bromo-6,9-epoxy-11,15-dihydroxyprost-13-enoic acid 2-propoxyethyl ester 249 mg of N-bromosuccinimide were added to a solution of 552 mg of PGF$_{2\alpha}$ 2-propoxyethyl ester (prepared as described in Reference Example 3) in a mixture of 10 ml of chloroform and 2.5 ml of tetrahydrofuran under a nitrogen atmosphere, and the reaction mixture was stirred for 2 hours at ambient temperature. The solution obtained was poured into water and extracted with diethyl ether. The extract was washed with water and an aqueous solution of sodium chloride, dried over magnesium sulphate and concentrated under reduced pressure. The residue was purified by column chromatography on silica gel using as eluent a mixture of ethyl acetate and cyclohexane (1:1) to give 506 mg of the title compound having the following physical characteristics.

TLC (developing solvent, chloroform:tetrahydrofuran: acetic acid=10:2:1): Rf=0.35;

IR (liquid film): $\nu = 3350, 1735, 970$ cm$^{-1}$;

NMR (CDCl$_3$ solution): $\delta = 5.65-5.40$ (2H, m), 4.75-3.20 (11H, m), 1.1-0.5 (6H, m).

EXAMPLE 6

(5Z,13E)-(9α,11α,15S)-6,9-Epoxy-11,15-dihydroxyprosta-5,13-dienoic acid 2-propoxyethyl ester [PGI$_2$ 2-propoxyethyl ester]

235 mg of (13E)-(5RS,6RS,9α,11α,15S)-5-bromo-6,9-epoxy-11,15-dihydroxyprost-13-enoic acid 2-propoxyethyl ester (prepared as described in Example 5) and 0.8 ml of DBU were stirred at 50°-60° C. for 3 hours under a nitrogen atmosphere. The solution obtained was cooled to 0°-5° C., 4 ml of 1 N hydrochloric acid and 4 ml of a phosphate buffer with a pH of 6.86, cooled to 0°-5° C., were added and the mixture was extracted with diethyl ether. The extract was dried over magnesium sulphate and concentrated under reduced pressure. The residue was purified by column chromatography on Florisil using as eluent a mixture of ethyl acetate and n-hexane (1:4) containing 0.1% v/v of triethylamine to give 136 mg of the title compound having the following physical characteristics.

TLC (developing solvent, diethyl ether:acetone=3:1 containing 0.1% of v/v of triethylamine; silica gel plate pre-treated with diethyl ether containing 5% v/v of triethylamine): Rf=0.45;

IR (liquid film): $\nu = 3350, 1730, 1700, 970$ cm$^{-1}$;

NMR (CDCl$_3$ solution): $\delta = 5.60-5.40$ (2H, m), 4.70-3.25 (10H, m), 1.05-0.60 (6H, m).

REFERENCE EXAMPLE 4

PGF$_{2\alpha}$ ethoxycarbonylmethyl ester 0.6 ml of triethylamine and 0.5 ml of pivaloyl chloride were added to a solution of 1.213 g of PGF$_{2\alpha}$ in 15 ml of methylene chloride, and the mixture was stirred for 10 minutes at ambient temperature. To the solution obtained were added 5.3 ml of ethyl glycolate and 3.3 ml of pyridine, and the reaction mixture was stirred for 2 hours at ambient temperature. The solution obtained was diluted with ethyl acetate, washed with 0.5 N hydrochloric acid, an aqueous solution of sodium bicarbonate and an aqueous solution of sodium chloride, dried over magnesium sulphate and concentrated under reduced pressure. The residue was purified by column chromatography on silica gel using as eluent a mixture of cyclohexane and ethyl acetate (1:2) to give 797 mg of the title compound having the following physical characteristics.

TLC (developing solvent, chloroform:tetrahydrofuran: acetic acid=10:2:1): Rf=0.20;

IR (liquid film): $\nu = 3350, 1740, 1140, 970$ cm$^{-1}$;

NMR (CDCl$_3$ solution): $\delta = 5.80-5.20$ (4H, m), 4.58 (2H, s), 4.50-3.75 (5H, m), 1.29 (3H, t), 1.05-0.75 (3H, m).

EXAMPLE 7

(13E)-(5RS,6RS,9α,11α,15S)-5-Bromo-6,9-epoxy-11,15-dihydroxyprost-13-enoic acid ethoxycarbonylmethyl ester 313 mg of N-bromosuccinimide were added, under a nitrogen atmosphere, to a solution of 716 mg of PGF$_{2\alpha}$ ethoxycarbonylmethyl ester (prepared as described in Reference Example 4) in a mixture of 12 ml of chloroform and 3 ml of tetrahydrofuran, and the mixture was stirred for 2 hours at ambient temperature. The solution obtained was then poured into water and extracted with diethyl ether. The extract was washed with water and an aqueous solution of sodium chloride, dried over magnesium sulphate and concentrated under reduced pressure. The residue was purified by column chromatography on silica gel using as eluent a mixture of ethyl acetate and cyclohexane (1:1) to give 614 mg of the title compound having the following physical characteristics.

TLC (developing solvent, chloroform:tetrahydrofuran: acetic acid = 10:2:1): Rf = 0.40;

IR (liquid film): $\sigma$ = 3400, 1740, 970 cm$^{-1}$;

NMR (CDCl$_3$ solution): $\delta$ = 5.65–5.40 (2H, m), 4.75–3.30 (7H, m), 4.58 (2H, s), 1.29 (3H, t), 1.05–0.75 (3H, m).

EXAMPLE 8

(5Z,13E)-(9$\alpha$,11$\alpha$,15S)-6,9-Epoxy-11,15-dihydroxyprosta-5,13-dienoic acid ethoxycarbonylmethyl ester [PGI$_2$ ethoxycarbonylmethyl ester]

A mixture of 287 mg of (13E)-(5RS,6RS,9$\alpha$,11$\alpha$,15S)-5-bromo-6,9-epoxy-11,15-dihydroxyprost-13-enoic acid ethoxycarbonylmethyl ester (prepared as described in Example 7) and 1 ml of DBU was stirred for 2.5 hours at 50°–60° C. under a nitrogen atmosphere. The solution obtained was cooled to 0° C.–5° C., 5 ml of 1 N hydrochloric acid and 5 ml of a phosphate buffer with a pH of 6.86, cooled to 0°–5° C., were added and the mixture was extracted with diethyl ether. The extract was dried over magnesium sulphate and concentrated under reduced pressure. The residue was purified by column chromatography on Florisil using as eluent a mixture of ethyl acetate and n-hexane (1:1) containing 0.1% v/v of triethylamine to give 181 mg of the title compound having the following physical characteristics.

TLC (developing solvent, diethyl ether:acetone = 3:1 containing 0.1% v/v of triethylamine; silica gel plate pre-treated with diethyl ether containing 5% v/v of triethylamine): Rf = 0.50;

IR (liquid film): $\nu$ = 3350, 1735, 1695, 970 cm$^{-1}$;

NMR (CDCl$_3$ solution): $\delta$ = 5.60–5.40 (2H, m), 4.60 (2H, s), 4.80–3.20 (6H, m), 1.30 (3H, t), 1.05–0.60 (3H, m).

By proceeding as described in Examples 7 and 8 but replacing the PGF$_{2\alpha}$ ethoxycarbonylmethyl ester used as starting material by PGF$_{2\alpha}$ 9-ethoxycarbonylnonyl ester (prepared as described in Example 5 of British Pat. No. 1,362,956) there was obtained (5Z,13E)-(9$\alpha$,11$\alpha$,15S)-6,9-epoxy-11,15-dihydroxyprosta-5,13-dienoic acid 9-ethoxycarbonylnonyl ester (PGI$_2$ 9-ethoxycarbonylnonyl ester) having the following physical characteristics.

TLC (developing solvent, diethyl ether:acetone = 3:1 containing 0.1% v/v of triethylamine; silica gel plate pre-treated with diethyl ether containing 5% v/v of triethylamine): Rf = 0.66;

IR (liquid film): $\nu$ = 3450, 1740, 1695, 1160, 975 cm$^{-1}$;

NMR (CDCl$_3$ solution): $\delta$ = 5.75–5.40 (2H, m), 4.75–3.50 (8H, m), 1.27 (3H, t), 1.00–0.65 (3H, m).

REFERENCE EXAMPLE 5

By proceeding as described in Example 1, but replacing the PGF$_{2\alpha}$ 2-(N,N-diethylamino)ethyl ester used as starting material by PGF$_{2\alpha}$ and PGF$_{2\alpha}$ 11,15-bis-(tetrahydropyran-2-yl)ether [i.e. (5Z,13E)-(9$\alpha$,11$\alpha$,15S)-9-hydroxy-11,15-bis(tetrahydropyran-2-yloxy)prosta-5,13-dienoic acid], respectively, there were obtained, respectively:

(a) (13E)-(5RS,6RS,9$\alpha$,11$\alpha$,15S)-5-bromo-6,9-epoxy-11,15-dihydroxyprost-13-enoic acid, having the following physical characteristics:

TLC (developing solvent, ethyl acetate:formic acid = 400:5): Rf = 0.31;

IR (liquid film): $\nu$ = 3400, 1710, 1440, 970 cm$^{-1}$;

NMR (CDCl$_3$ solution): $\delta$ = 5.65–5.38 (2H, m), 4.96 (3H, broad s), 4.70–4.38 (1H, m), 4.30–3.70 (4H, m), 1.01–0.70 (3H, m); and (b) (13E)-(5RS,6RS,9$\alpha$,11$\alpha$,15S)-5-bromo-6,9-epoxy-11,15-bis(tetrahydropyran-2-yloxy)prost-13-enoic acid having the following physical characteristics.

TLC (developing solvent, ethyl acetate:formic acid = 400:5): Rf = 0.55;

IR (liquid film): $\nu$ = 1710, 1440, 1020, 980 cm$^{-1}$;

NMR (CDCl$_3$ solution): $\delta$ = 8.70 (1H, broad s), 5.70–5.25 (2H, m), 4.80–4.45 (3H, m), 4.23–3.25 (8H, m), 1.02–0.70 (3H, m).

EXAMPLE 9

By proceeding as described in Reference Example 1, but replacing the PGF$_{2\alpha}$ used as starting material by (13E)-(5RS,6RS,9$\alpha$,11$\alpha$,15S)-5-bromo-6,9-epoxy-11,15-dihydroxyprost-13-enoic acid (prepared as described in Reference Example 5) and replacing the 2-(N,N-diethylamino)-ethanol by octane-1,8-diol and 2-(N,N-dimethylamino)-ethanol, respectively, there were obtained, respectively:

(a) (13E)-(5RS,6RS,9$\alpha$,11$\alpha$,15S)-5-bromo-6,9-epoxy-11,15-dihydroxyprost-13-enoic acid 8-hydroxyoctyl ester having the following physical characteristics.

TLC (developing solvent, ethy acetate): Rf = 0.31;

IR (liquid film): $\nu$ = 2970, 2950, 2870, 1940, 1460 cm$^{-1}$;

NMR (CDCl$_3$ solution): $\delta$ = 5.62–5.43 (2H, m), 4.65–4.35 (1H, m), 4.06 (2H, t), 3.61 (2H, t), 4.40–3.70 (4H, m); and (b) (13E)-(5RS,6RS,9$\alpha$,11$\alpha$,15S)-5-bromo-6,9-epoxy-11,15-dihydroxyprost-13-enoic acid 2-(N,N-dimethylamino)ethyl ester having the following physical characteristics.

TLC (developing solvent, acetone): Rf = 0.08;

IR (liquid film): $\nu$ = 2970, 2950, 2875, 1740, 1580, 1460, 1180 cm$^{-1}$;

NMR (CDCl$_3$ solution): $\delta$ = 5.60–5.44 (2H, m), 4.21 (2H, t), 2.67 (2H, t), 4.65–4.40 (1H, m), 4.40–3.60 (6H, m), 2.34 (6H, s).

By proceeding as described in Reference Example 1 but replacing the PGF$_{2\alpha}$ by (13E)-(5RS,6RS,9$\alpha$,11$\alpha$,15S)-5-bromo-6,9-epoxy-11,15-bis(tetrahydropyran-2-yloxy)prost-13-enoic acid [prepared as described in Reference Example 5(b)] and replacing the 2-(N,N-diethylamino)ethanol by ethylene glycol, there was obtained:

(c) (13E)-(5RS,6RS,9$\alpha$,11$\alpha$,15S)-5-bromo-6,9-epoxy-11,15-bis(tetrahydropyran-2-yloxy)prost-13-enoic acid 2-hydroxyethyl ester having the following physical characteristics:

TLC (developing solvent, benzene:ethyl acetate = 2:1): RF = 0.35;

IR (liquid film): $\nu$ = 3450, 1735, 1165, 1080, 1040, 1030, 980 cm$^{-1}$;

NMR (CDCl$_3$ solution): $\delta$ = 5.65–5.30 (2H, m), 4.75–4.58 (2H, m), 4.58–4.43 (1H, m), 4.28–4.12 (2H, m), 3.85–3.73 (2H, m), 0.88 (3H, t).

EXAMPLE 10

(13E)-(5RS,6RS,9α,11α,15S)-5-Bromo-11,15-dihyroxyprost-13-enoic acid 2-hydroxyethyl ester A solution of 1.15 g of (13E)-(5RS,6RS,9α,11α, 15S)-5-bromo-6,9-epoxy-11,15-bis(tetrahydropyran-2-yloxy)prost-13-enoic acid 2-hydroxyethyl ester [prepared as described in Example 9(c)] in 20 ml of a mixture of acetic acid, water and tetrahydrofuran (3:1:1) was stirred for 4 hours at 40° C. The solution obtained was poured into an aqueous solution of sodium bicarbonate (prepared by dissolving 20 g of sodium bicarbonate in 100 ml of water), and extracted with chloroform. The extract was dried over sodium sulphate, and concentrated under reduced pressure. The residue was purified by column chromatography on silica gel using as eluent a mixture of benzene, diethyl ether and tetrahydrofuran (1:1:1) to give 604 mg of the title compound having the following physical characteristics:

TLC (developing solvent, benzene:diethyl ether: tetrahydrofuran=1:1:1): Rf=0.35 and 0.40;

IR (liquid film): $\nu$=3400, 1735, 1460, 1080, 975 cm$^{-1}$;

NMR (CDCl$_3$ solution): $\delta$=5.58-5.40 (2H, m), 4.60-4.40 (1H, m), 4.30-4.12 (2H, m), 4.12-3.86 (2H, m), 3.86-3.70 (2H, m), 3.35-2.90 (3H, m), 0.88 (3H, t).

EXAMPLE 11

By proceeding as described in Example 2, but replacing the (3E)-(5RS,6RS,9α,11α,15S)-5-bromo-6,9-epoxy-11,15-dihydroxyprost-13-enoic acid 2-(N,N-diethylamino)-ethyl ester used as starting material by (13E)-(5RS,6RS,9α,11α,15S)-5-bromo-6,9-epoxy-11,15-dihydroxyprost-13-enoic acid 8-hydroxyoctyl ester [prepared as described in Example 9(a)], (13E)-(5RS,6RS,9α,11α,15S)-5-bromo-6,9-epoxy-11,15-dihydroxyprost-13-enoic acid 2-(N,N-dimethylamino)ethyl ester [prepared as described in Example 9(b)], and (13E)-(5RS,6RS,9α,11α,15S)-5-bromo-11,15-dihydroxyprost-13-enoic acid 2-hydroxyethyl ester (prepared as described in Example 10), respectively, there were obtained, respectively:

(a) (5Z,13E)-(9α,11α,15S)-6,9-epoxy-11,15-dihydroxyprosta-5,13-dienoic acid 8-hydroxyoctyl ester [PGI$_2$ 8-hydroxyoctyl ester] having the following physical characteristics:

TLC (developing solvent, acetone:diethyl ether=4:1; silica gel plate pre-treated with a 5% v/v solution of triethylamine in diethyl ether); Rf=0.55;

IR (liquid film): $\nu$=2950, 2875, 1740, 1720, 1700 1650, 1460, 1050 cm$^{-1}$;

NMR (benzene-d$_6$ solution): $\delta$=5.83-5.23 (2H, qq), 4.09 (2H, t), 3.52 (2H, t), 4.40-3.40 (6H, m).

(b) (5Z,13E)-(9α,11α,15S)-6,9-epoxy-11,15-dihydroxyprosta-5,13-dienoic acid 2-(N,N-dimethylamino)ethyl ester [PGI$_2$ 2-(N,N-dimethylamino)-ethyl ester] having the following physical characteristics:

TLC (developing solvent, acetone; silica gel plate pre-treated with a 5% v/v solution of triethylamine in diethyl ether): Rf=0.77;

IR (liquid film): $\nu$=2970, 2950, 2875, 1740, 1700, 1660, 1460, 1170, 1050 cm$^{-1}$;

NMR (benzene-d$_6$ solution): $\delta$=5.82-5.26 (2H, qq), 4.11 (2H, t), 4.40-3.10 (6H, m), 2.04 (6H, s); and (c) (5Z,13E)-(9α,11α,15S)-6,9-epoxy-11,15-dihydroxyprosta-5,13-dienoic acid 2-hydroxyethyl ester [PGI$_2$ 2-hydroxyethyl ester] having the following physical characteristics:

TLC (developing solvent, diethyl ether:acetone=3:1); silica gel plate pre-treated with a 5% v/v solution of triethylamine in diethyl ether): Rf=0.58;

IR (liquid film): $\nu$=3350, 1740, 1695, 1090, 1050, 975 cm$^{-1}$;

NMR (CDCl$_3$ solution): $\delta$=5.57-5.40 (2H, m), 4.10-3.60 (3H, m), 4.67-4.45 (1H, m), 4.25-4.10 (2H, m), 3.85-3.70 (2H, m), 3.50-3.13 (3H, m).

The present invention includes within its scope pharmaceutical compositions which comprise at least one new therapeutically useful compound of general formula II, or cyclodextrin clathrate thereof or, when R$^1$ in general formula II represents a group

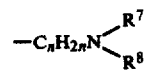

in which n, R$^7$ and R$^8$ are as hereinbefore defined, non-toxic acid addition salts thereof, together with a pharmaceutical carrier or coating. In clinical practice the new compounds of the present invention will normally be administered parenterally, vaginally or rectally.

Preparations according to the invention for parenteral administration include sterile aqueous or non-aqueous solutions, suspensions or emulsions. Examples of non-aqueous solvents or suspending media are propylene glycol, polyethylene glycol, vegetable oils such as olive oil, and injectable organic esters such as ethyl oleate. These compositions may also include adjuvants such as preserving, wetting, emulsifying and dispersing agents. They may be sterilised, for example, by filtration through a bacteria-retaining filter, by incorporation of sterilising agents in the compositions or by irradiation. They may also be manufactured in the form of sterile solid compositions, which can be dissolved in sterile water or some other sterile injectable medium immediately before use.

Solid compositions for vaginal administration include pessaries formulated in manner known per se and containing one or more of the active compounds.

Solid compositions for rectal administration include suppositories formulated in manner known per se and containing one or more of the active compounds.

The percentage of active ingredient in the compositions of the invention may be varied, it being necessary that it should constitute a proportion such that a suitable dosage for the therapeutic effect desired shall be obtained. Obviously several unit dosage forms may be administered at about the same time. In general, the preparations should normally contain at least 0.025% by weight of active substance when required for administration by injection. The dose employed depends upon the desired therapeutic effect, the route of administration and the duration of the treatment.

In the human adult, each dose per person is generally between 0.05 and 500 $\mu$g by parenteral administration in the treatment of hypertension, between 0.05 and 500 $\mu$g by parenteral administration in the treatment of disorders of the peripheral circulation, and between 0.05 and 500 $\mu$g by parenteral administration in the prevention and treatment of cerebral thrombosis, myocardial infarction and arteriosclerosis.

The following Example illustrates pharmaceutical compositions according to the invention.

EXAMPLE 12

(5Z,13E)-(9α,11α,15S)-6,9-Epoxy-11,15-dihydroxyprosta-5,13-dienoic acid 2-(N,N-diethylamino)ethyl ester (500 μg) was dissolved in ethanol (5 ml). The solution was then sterilized by passage through a bacteria-retaining filter and placed in 0.1 ml portions in 1 ml ampoules, to give 10 μg of (5Z,13E)-(9α,11α,15S)-6,9-epoxy-11,15-dihydroxyprosta-5,13-dienoic acid 2-(N,N-diethylamino)ethyl ester per ampoule. The ampoules were sealed. The contents of an ampoule diluted to a suitable volume, e.g. with 1 ml of tris-HCl-buffer solution (pH 8.6), gave a solution ready for administration by injection.

We claim:

1. A prostaglandin analogue of the general formula:

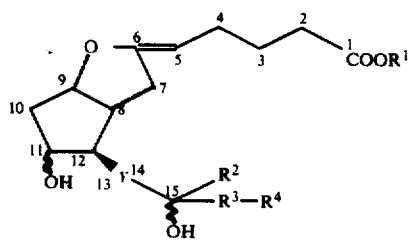

wherein Y represents ethylene or trans-vinylene, $R^1$ represents a group $-C_mH_{2m}COOR^5$, $-C_nH_{2n}OR^6$ or

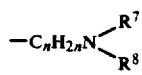

in which $R^5$ represents a straight- or branched-chain alkyl group containing from 1 to 4 carbon atoms, $R^6$ represents a hydrogen atom or a straight- or branched-chain alkyl group containing from 1 to 4 carbon atoms, $R^7$ and $R^8$, which may be the same or different, each represents a straight- or branched-chain alkyl group containing from 1 to 4 carbon atoms, m represents an integer of from 1 to 12 and n represents an integer of from 2 to 12; $R^2$ represents a hydrogen atom or a methyl or ethyl group; $R^3$ represents a single bond or a straight- or branched-chain alkylene group containing from 1 to 4 carbon atoms; $R^4$ represents a hydrogen atom, a straight- or branched-chain alkyl group containing from 1 to 8 carbon atoms, a cycloalkyl group containing from 4 to 7 carbon atoms in the ring, which may be unsubstituted or substituted by at least one straight- or branched-chain alkyl group containing from 1 to 8 carbon atoms, or represents a phenyl or phenoxy group which may be unsubstituted or substituted by at least one chlorine atom, trifluoromethyl group or alkyl group containing from 1 to 3 carbon atoms; the wavy line ⌇⌇⌇ attached to the carbon atoms in positions 11 and 15 represents α- or β-configuration or mixtures thereof; and the double bond between $C_5-C_6$ is Z, and, when $R^1$ represents a group

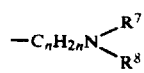

in which n, $R^7$ and $R^8$ are as hereinbefore defined, non-toxic acid addition salts thereof.

2. A prostaglandin analogue according to claim 1 wherein $R^1$ represents a group $-C_mH_{2m}COOR^5$ wherein m represents an integer from 1 to 9 and $R^5$ is as defined in claim 1.

3. A prostaglandin analogue according to claim 2 wherein $R^5$ represents ethyl.

4. A prostaglandin analogue according to claim 1 wherein $R^1$ represents a group $-C_nH_{2n}OR^6$ wherein n represents an integer from 2 to 8 and $R^6$ is as defined in claim 1.

5. A prostaglandin analogue according to claim 4 wherein $R^6$ represents a hydrogen atom or n-propyl.

6. A prostaglandin analogue according to claim 1 wherein $R^1$ represents a group

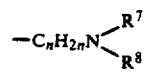

wherein n represents 2 and $R^7$ and $R^8$ are as defined in claim 1.

7. A prostaglandin analogue according to claim 6 wherein $R^7$ and $R^8$ each represent methyl or ethyl.

8. A prostaglandin analogue according to claim 1 wherein Y represents trans-vinylene.

9. A prostaglandin analogue according to claim 1 wherein $R^2$ represents a hydrogen atom.

10. A prostaglandin analogue according to claim 1 wherein the grouping $-R^3-R^4$ represents n-pentyl, 1-methylpentyl, 2-methylpentyl, 3-methylpentyl, 4-methylpentyl, 1,1-dimethylpentyl, 1,2-dimethylpentyl, 1,4-dimethylpentyl, 1-ethylpentyl, 2-ethylpentyl, 1-propylpentyl, 2-propylpentyl, n-hexyl, 1-methylhexyl, 2-methylhexyl, 1,1-dimethylhexyl, 1-ethylhexyl, 2-ethylhexyl, n-heptyl, 2-ethylheptyl, n-nonyl, n-undecyl, cyclobutyl, (1-propyl)cyclobutyl, (1-butyl)cyclobutyl, (1-pentyl)cyclobutyl, (2-propyl)cyclobutyl, (3-ethyl)cyclobutyl, (3-propyl)cyclobutyl, cyclopentyl, 1-cyclopentylethyl, 2-cyclopentylethyl, 2-cyclopentylpropyl, (3-ethyl)cyclopentyl, (3-propyl)cyclopentyl, (3-butyl)cyclopentyl, (1-methyl-3-propyl)cyclopentyl, (2-methyl-3-propyl)cyclopentyl, cyclohexyl, (3-ethyl)cyclohexyl, (4-methyl)cyclohexyl, (4-ethyl)cyclohexyl, (4-propyl)cyclohexyl, (2,6-dimethyl)cyclohexyl, cyclohexylmethyl, (1-methyl)cyclohexylmethyl, 1-cyclohexylethyl, 2-cyclohexylethyl, (1-methyl-1-cyclohexyl)ethyl, 1-cycloheptylethyl, phenyl, benzyl, α-phenylethyl, β-phenylethyl, phenoxymethyl, (3-chlorophenoxy)methyl, (4-chlorophenoxy)methyl or (3-trifluoromethylphenoxy)methyl.

11. A prostaglandin analogue according to claim 1 wherein the grouping $-R^3-R^4$ represents n-pentyl.

12. A prostaglandin analogue according to claim 1 wherein the hydroxy groups attached to the C-11 and C-15 carbon atoms in general formula II depicted in claim 1 are in α-configuration.

13. A prostaglandin analogue according to claim 1 which is (5Z,13E)-(9α,11α,15S)-6,9-epoxy-11,15-dihydroxyprosta-5,13-dienoic acid 2-(N,N-diethylamino)-ethyl ester.

14. A prostaglandin analogue according to claim 1 which is (5Z,13E)-(9α,11α,15S)-6,9-epoxy-11,15-dihydroxyprosta-5,13-dienoic acid 5-hydroxypentyl ester.

15. A prostaglandin analogue according to claim 1 which is (5Z,13E)-(9α,11α,15S)-6,9-epoxy-11,15-dihydroxyprosta-5,13-dienoic acid 2-propoxyethyl ester.

16. A prostaglandin analogue according to claim 1 which is (5Z,13E)-(9α,11α,15S)-6,9-epoxy-11,15-dihydroxyprosta-5,13-dienoic acid ethoxycarbonylmethyl ester.

17. A prostaglandin analogue according to claim 1 which is (5Z,13E)-(9α,11α,15S)-6,9-epoxy-11,15-dihydroxyprosta-5,13-dienoic acid 9-ethoxycarbonylnonyl ester.

18. A prostaglandin analogue according to claim 1 which is (5Z,13E)-(9α,11α,15S)-6,9-epoxy-11,15-dihydroxyprosta-5,13-dienoic acid 8-hydroxyoctyl ester.

19. A prostaglandin analogue according to claim 1 which is (5Z,13E)-(9α,11α,15S)-6,9-epoxy-11,15-dihydroxyprosta-5,13-dienoic acid 2-(N,N-dimethylamino)ethyl ester.

20. A prostaglandin analogue according to claim 1 which is (5Z,13E)-(9α,11α,15S)-6,9-epoxy-11,15-dihydroxyprosta-5,13-dienoic acid 2-hydroxyethyl ester.

21. A pharmaceutical composition useful in the treatment of hypertension and disorders of the peripheral circulation and in the prevention and treatment of cerebral thrombosis, myocardial infarction, and arteriosclerosis which comprises as active ingredient, an effective amount of a prostaglandin analogue as claimed in claim 1 or, when $R^1$ represents a group

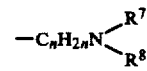

in which n, $R^7$ and $R^8$ are as defined in claim 1, a non-toxic acid addition salt thereof, in association with a pharmaceutical carrier or coating.

* * * * *